United States Patent
Lindholm

(10) Patent No.: US 6,981,466 B2
(45) Date of Patent: Jan. 3, 2006

(54) MILKING

(75) Inventor: Leif Lindholm, Rönninge (SE)

(73) Assignee: Delaval Holding AB, Tumba (SE)

( * ) Notice: Subject to any disclaimer, the term of this patent is extended or adjusted under 35 U.S.C. 154(b) by 0 days.

(21) Appl. No.: 10/764,948

(22) Filed: Jan. 26, 2004

(65) Prior Publication Data

US 2004/0168644 A1    Sep. 2, 2004

(30) Foreign Application Priority Data

Jan. 31, 2003    (EP) .................................. 03250605

(51) Int. Cl.
    *A01J 5/00*    (2006.01)
    *A01J 9/00*    (2006.01)
(52) U.S. Cl. .................. 119/14.02; 119/14.17
(58) Field of Classification Search ............. 119/14.02, 119/14.08, 14.17, 14.46, 14.54
See application file for complete search history.

(56) References Cited

U.S. PATENT DOCUMENTS

| | | | |
|---|---|---|---|
| 3,841,756 A | 10/1974 | Grochowicz | |
| 4,385,590 A * | 5/1983 | Mortensen | ............... 119/14.01 |
| 4,437,346 A | 3/1984 | Kummer | |
| 4,574,630 A | 3/1986 | Icking et al. | |
| 5,161,483 A * | 11/1992 | Moskvin | .................. 119/14.17 |

FOREIGN PATENT DOCUMENTS

| | | |
|---|---|---|
| EP | 0 385 539 A2 | 9/1990 |
| EP | 0 564 023 A1 | 10/1993 |
| EP | 0 665 434 A1 | 8/1995 |
| EP | 0 666 475 A2 | 8/1995 |
| GB | 2 113 856 A | 8/1983 |
| WO | WO 01/74150 A1 | 10/2001 |
| WO | WO 02/069697 A1 | 9/2002 |

* cited by examiner

Primary Examiner—Robert P. Swiatek
(74) Attorney, Agent, or Firm—James H. Marsh, Jr.; Stinson Morrison Hecker LLP

(57) ABSTRACT

A milk metering apparatus having a metering chamber 7 which is repeatedly filled and emptied many times in the course of milking an animal is provided with a probe 15 which extends down into the metering chamber 7 and which includes a sampling tube as well as conductivity and light absorption sensors. Milk samples can be taken and conductivity and light absorption measurements can be made during each filling and emptying cycle so that data from the sample analysis and the measurements over the whole period of milking can be compared with corresponding data from previous milkings of the same animal thereby providing valuable information for herd management purposes.

57 Claims, 3 Drawing Sheets

MILKING

FIELD OF THE INVENTION

This invention is concerned with the milking of animals, especially cows.

BACKGROUND OF THE INVENTION

It has been known for many years to measure and record the quantity of milk obtained from an animal during each milking. It is also well known to analyse the milk quality and/or composition by sensing certain properties of the milk, such as electrical conductivity, somatic cell count, temperature, light absorption or transmission characterics which may be indicative of fat content for example, and protein content. The results of the quantity measurements and analysis of the milk can provide important information about the health and well-being of an animal, and is of valuable assistance to herd management. For example, mastitis and other infections may be detected at an early stage before milk quality become seriously impaired, automatic separation of foremilk can be implemented, the course of the lactation period can be automatically monitored, and appropriate amounts of food and feed concentrates can be calculated to ensure a well balanced diet, all of these factors making important contributions to efficient milk production in terms of yield and quality.

A milk meter currently manufactured and marketed by DeLaval International AB is based on the milk meter described in GB-A-2113856A and includes a metering chamber defined within a measuring container supported by a strain gauge. The chamber has a milk inlet and a milk outlet which is controlled by a valve so that the metering chamber is repeatedly filled and emptied during the milking of an animal. The milk outlet valve is opened when a predetermined amount of milk has collected in the chamber, the predetermined amount being dependent on the rate of milk flow into the metering chamber, and the valve being closed again after a certain time. A container for collecting a sample may be attached to the milk meter to receive a portion of the milk discharged from the metering chamber each time it is emptied. This known milk meter provides an accurate measurement of the milk quantity, but analysis to determine the quality and/or composition of the milk has to be carried out separately on the collected sample after completion of milking.

In U.S. Pat. No. 3,841,756 there is described a milking parlour in which there is provided for each milking stall a milk analysing unit consisting of a container in which all the milk obtained from an animal during a milking is collected and the weight of the milk is measured. Inserted in the container of the analysing unit are a leukocyte sensor and a butterfat sensor, the former sensor having electrodes for sensing the electrical conductivity of the milk, and the latter sensor having an infrared light transmitter and a photocell for measuring the infrared light absorption property of the milk. The results of the quantity, leukocyte content and butterfat content measurements are recorded in the form of a printout. This analysis unit provides information on the milk quality/composition as well as the quantity of milk let down by each animal, but the ability to produce just one set of values for each milking severely limits the extent to which the recorded data can be utilised. In addition to changes which may occur from one milking to the next, variations in milk quality/composition over the course of a single milking can reveal information of valuable significance to herd management decision making. Furthermore, comparison of data obtained for milk collected from respective udder quarters can be helpful also, such as in the detection of subclinical mastitis.

EP-A-0385539 describes an automatic milking apparatus in which the teat cups are connected to respective milk meters. Each milk meter has a measuring chamber with a milk inlet and a milk outlet controlled by respective valves. The inlet and outlet valves are controlled so that the measuring chamber is repeatedly filled to a predetermined level and emptied, the number of filling and emptying cycles being counted by a computer to determine the quantity of milk obtained from each quarter of the udder of the animal. Each milk meter includes an electrical conductivity sensor for detecting milk effected by mastitis, the computer controlling a valve downstream of the metering chamber so that infected milk discharged from the metering chamber is diverted away from the main milk tank. This arrangement is useful for separating milk of unacceptable quality, but there is no provision for recording data relevant to the milk quality/composition to permit comparison over the course of a milking and from one milking to the next milking.

EP-A-0564023 describes a milking plant including milk meters of essentially the same form as described in EP-A-0385539, but there is no conductivity sensor or diverter valve for separating infected milk. Downstream of the milk meter is a sampling device. Filling and emptying the measuring chamber of the milk meter is repeated just a few times during one milking. During at least a selected number of emptying phases a small fraction of the milk discharged from the measuring chamber is diverted to the sampling device so that e.g. about 1% of the milk obtained from the cow is collected in a collecting element. With this arrangement a single sample is collected for a complete milking and it is not possible to compare analysis results for samples taken at particular stages of successive milkings or at different stages of the same milking.

There is disclosed in EP-A-0665434 and EP-A-0666475 milking installations in which a milk analyser is located downstream of a milk quantity meter in a milk line between a milk pump and a milk tank. A display screen displays the milk quantity determined by the quantity meter as well as the fat content and the albumin content determined by the milk analyser. This equipment is not able to discriminate between property values relating to milk quality or composition at discrete stages of a milking of a animal.

SUMMARY OF THE INVENTION

The present invention addresses the shortcomings of the prior art as discussed above and in accordance with one aspect the invention there is provided a method of milking an animal comprising the steps of directing milk collected from the udder of the animal into a metering chamber which is repeatedly filled and emptied during the milking procedure, checking the quality and/or composition of the milk collected in the metering chamber, and counting the number of filling and emptying cycles of the metering chamber, characterised in that during each of at least several cycles of filling and emptying the metering chamber the number of respective filling and emptying cycle is recorded, a milk sample is removed from the metering chamber for analysis, and/or at least one property of the milk in the metering chamber is sensed and recorded, the at least one property including electrical conductivity, a light absorption characteristic, and/or temperature.

Milk samples removed from the metering chamber can be analysed to determine the somatic cell count, fat content, protein content, urea content and or enzyme, for example NAGase (N-acetyl-D-glucosaminidase) content.

According to another aspect the invention provides a milk metering apparatus comprising a metering chamber into which milk from an udder of an animal is delivered in the course of milking the animal, the metering chamber having a milk inlet and a milk outlet for repeated filling and emptying of the metering chamber during the milking procedure, the number of filling and emptying cycles being counted for determination of the milk quantity, and a sampling duct communicating with the interior of the metering chamber for removal of milk samples from the metering chamber during respective filling and emptying cycles. Alternatively or additionally to the sampling duct there is at least one sensor for sensing a property of the milk in the metering chamber, the milk property being electrical conductivity, a light absorption or transmission characteristic, and/or temperature, and recording means which records values of the at least one property sensed for comparison with corresponding sensed and recorded means.

The milk sample can be withdrawn from the metering chamber through a tube, e.g. a suction tube, the tube defining the sampling duct and extending downwardly into the metering chamber. A suction device is preferably connected to the sampling duct and is operable for withdrawing a milk sample through the sampling duct from metering chamber by suction. An analyser may be connected to the sampling duct so that milk samples removed from the metering chamber are delivered directly to the analyser for analysis. Alternatively, a sample collecting device can be connected to the milk sampling duct, milk samples removed from the metering chamber being delivered into sample collection containers for laboratory analysis.

There can be provided in the metering chamber either instead of or in addition to the sampling tube, at least one sensor for sensing a property of the milk indicative of quality and/or composition, in particular electrical conductivity, a light absorption or transmission characteristic or temperature. Some properties of milk, the temperature for instance, can change quite rapidly after the milk has left the udder and sensing these properties in the metering chamber allows them to be measured and recorded very soon after the milk has been removed from the udder and before significant changes have had time to occur. For sensing electrical conductivity electrodes, e.g. carried on a probe extending into the metering chamber are preferred, and for sensing a light absorption characteristic a sensor comprising a light source, such as light emitting diode, and a light detecting device, such as a photocell, again carried by a probe extending down into the metering chamber, is preferred. Conveniently the electrodes, light source and light detecting device are provided on the same probe which can also incorporate the suction tube for sample removal from the metering chamber. Alternatively two or more probes can be employed, for example, one for each milk property to be sensed in the metering chamber.

The apparatus preferably includes recording means such as a computer for recording the property values obtained from analysis of the milk samples and/or by direct measurement on the milk in the metering chamber, and for recording the number of the filling and emptying cycles during which the respective samples were taken from the metering chamber and/or the milk property values were sensed in the metering chamber. Recorded values relevant to the quality/composition of the milk collected in the metering chamber during a selected filling and emptying cycle can be compared with the corresponding recorded values related to milk collected in the metering chamber during a corresponding filling and emptying cycle during a previous milking of the same animal, and/or with the corresponding recorded values for milk collected in the metering chamber during an earlier filling and emptying cycle during the same milking. Preferably the recording means also records the time of milking and the interval since the immediately preceding milking of the animal. It has been observed that milk property values, such as the electrical conductivity of foremilk and somatic cell count are influenced by the time interval that has elapsed between a milking and the immediately preceding milking.

It is preferable that the number of filling and emptying cycles of the metering chamber per milking is relatively large and is appropriate, therefore, that the emptying of the metering chamber is initiated in response to a predetermined amount of milk not more than about one liter or about 0.5 kg, more especially 0.2 liters or 0.1 kg, having collected in the metering chamber. The emptying of the metering chamber is suitably commenced when the amount of milk collected therein reaches a value in the range of 20 g to 400 g, more particularly 50 g to 150 g, the metering chamber having a milk collecting capacity in the same range. This means that for a typical cow the number of filling and emptying cycles for milking can be more than 100, for example 150 to 250. Emptying can be commenced in response to different predetermined amounts of milk being collected dependent on the milk flow rate into the metering chamber.

With the metering chamber having a relatively small capacity in relation to the total quantity of milk for one milking so that the metering chamber is filled and emptied many times during one milking, a large amount of data can be collected from the samples taken and/or measurements made by means of the sensors located in the metering chamber and it can also be recorded at which time, or the stage in the course of milking, i.e. during which filling and emptying cycle, each analysed sample was taken and/or the respective readings were taken by means of the sensors. It is possible for a sample to be taken and/or milk property values to be sensed and recorded during each and every filling and emptying cycle of the metering chamber to maximise the data collection. This can allow all the samples to be collected and mixed to provide a complete sample for the milking of the animal that is proportional and truly representative of all the milk collected and measured in the metering chamber during that milking. If preferred the analysis can be performed on the complete mixed sample. However, it may be sufficient for samples to be taken and/or milk property values to be sensed by the sensors and recorded by the recording means less often, such as every other filling and emptying cycle, possibly once in every four filling and emptying cycles, or perhaps once in every ten filling and emptying cycles. Control means which controls the sample taking and/or sensing and recording of milk property values may be programmable to permit selection of the frequency of sample taking and/or property value sensing and recording according to requirements. Alternatively the frequency of the filling and emptying cycles during which a milk sample is taken and/or property values are sensed and recorded can be selected automatically, such as in dependence upon the results of the analysis of a sample taken from the metering chamber and/or the milk property values sensed and recorded either during a previous milking of the animal, or during the same milking procedure, in particular during the early stages of the milking procedure. Increasing the frequency at which samples are taken and/or property values are sensed, such as in response to unexpected measurement values are due to an isolated event or are indicative of a trend. In addition it is possible for samples to be taken and/or property value readings to be performed more than once during a filling or emptying cycle and/or for it to be selected at which specific time or times it is done during the filling and emptying cycle. It is also possible for the frequency of sample taking and/or property value sensing and recording to be changed during the course of the milking so that, for example, the sample taking and/or data recording may be performed more frequently during an initial part of the milking period than during a subsequent part of the milking period or vice versa.

In a particularly expedient embodiment the metering chamber is defined within a measuring container supported by a weighing device, specifically a strain gauge device, and means are provided to cause a milk sample to be removed from the metering chamber in response to a signal from the weighing device. With such an arrangement it can easily be assured that samples are taken at a set point during the filling and emptying cycles, that is when a certain amount of milk has been collected in the metering chamber. It is also possible for sample to be taken at two or more specific times during a filling phase, for example at the beginning, in the middle and at the end of the filling phase as determined by the strain gauge.

Although the milk collected from all the teats of the animal, that is from all four udder quarters in the case of an animal having four teats, such as a cow, can be directed into the metering chamber, it is preferable for each teat cup to be connected to a respective metering chamber, so that the quantity of milk produced by each udder quarter is separately recorded, and data relating to the milk quality/composition is also recorded separately for each quarter. Comparing milk data relating to different quarters of the same animal can be useful in identifying at an early stage physiological changes occurring in one quarter, such as the onset of mastitis.

DESCRIPTION OF THE DRAWINGS

To assist a clear understanding of the invention it is further described below with reference being made to the accompanying drawings in which.

DESCRIPTION OF THE PREFERRED EMBODIMENTS

Figure 1:
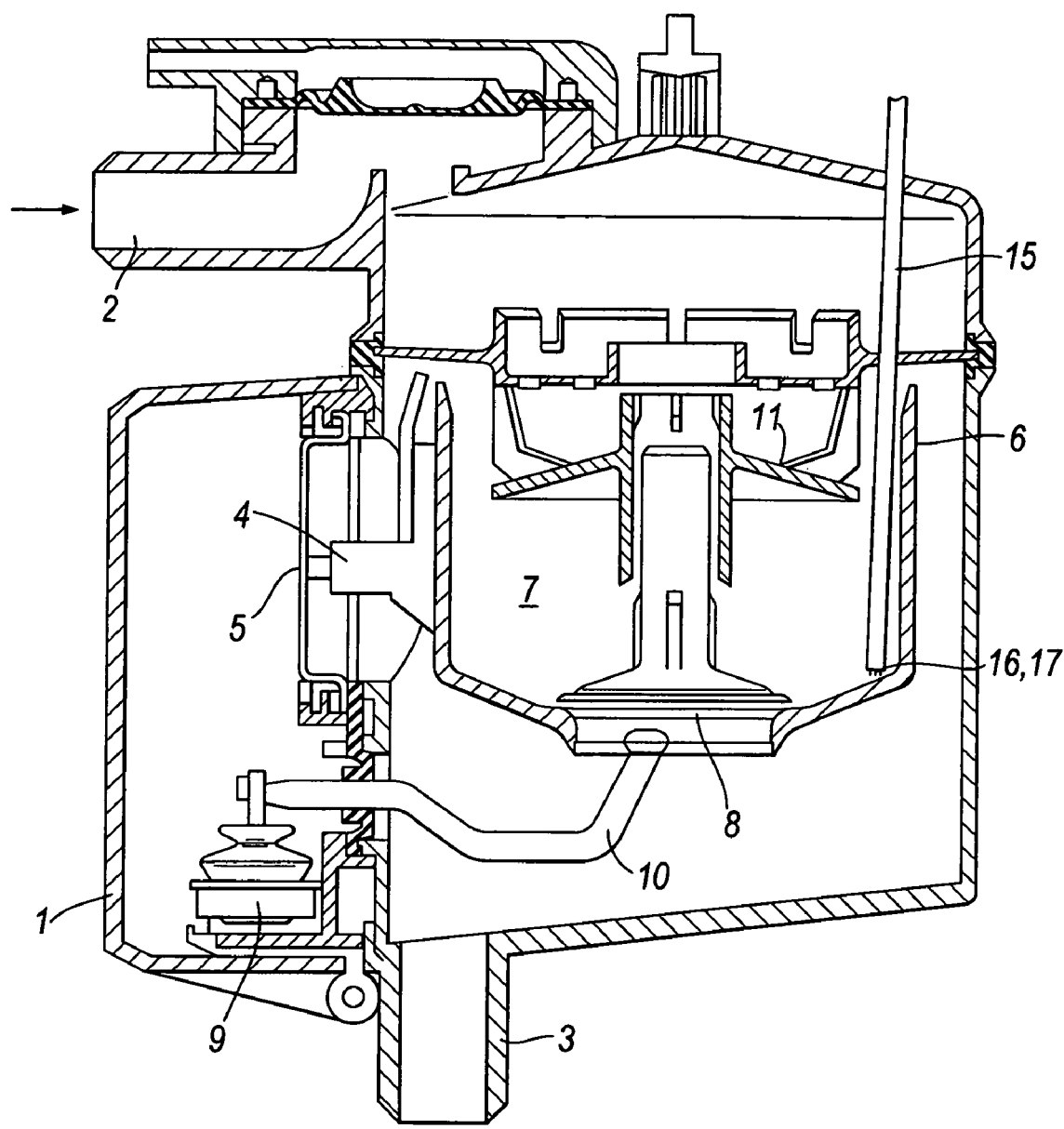
FIG. 1 is a schematic cross-section illustrating a milk metering apparatus according to the invention.

The milk meter shown in FIG. 1 is basically the same as the DeLaval milk meter MM15 currently manufactured and sold by DeLaval International AB. It comprises a casing 1 with a milk inlet 2 for connection of a milk tube attached to a teat cup, and a milk outlet 3 for connection to a milk line e.g. leading to a milk tank or optionally to a waste tank for collection of milk not intended for consumption. Located within the casing 1 and supported by an arm 4 fastened to strain gauge 5 is a measuring container 6 in which there is defined a metering chamber 7. The container 6 has an open top forming a milk inlet, and an outlet opening at the bottom controlled by a valve 8 which is coupled to a valve actuator 9 by an arm 10. A stationary baffle member 11, supported from the casing 1, is positioned within the measuring chamber 7 to ensure gentle flow of milk into the metering chamber so as not to disrupt the metering function. The control electronics associated with the strain gauge continuously registers the weight of milk in the metering chamber and when it reaches a predetermined amount, e.g. 90, 70 or 60 grms depending upon the milk flow rate, the valve actuator 9 is activated to open the outlet valve 8 so that the milk is emptied out of the metering chamber 7. After a certain time has elapsed, e.g. 0.5 sec to 2.5 sec depending on the milk flow rate, the valve is closed again and refilling of the metering chamber commences. The cycle of filling and emptying the measuring chamber is repeated many times, in particular around 100 to 200 times, during a single milking procedure for one animal. The exact number of filling and emptying cycles of course depends on the quantity of milk obtained from the animal. The control unit measures the weight of milk collecting during each filling phase of the metering chamber, and based on the rate of increase in weight during filling calculates the weight of milk which flows into the metering chamber during each emptying phase, and the total quantity of milk is recorded by the control unit.

Figure 3:
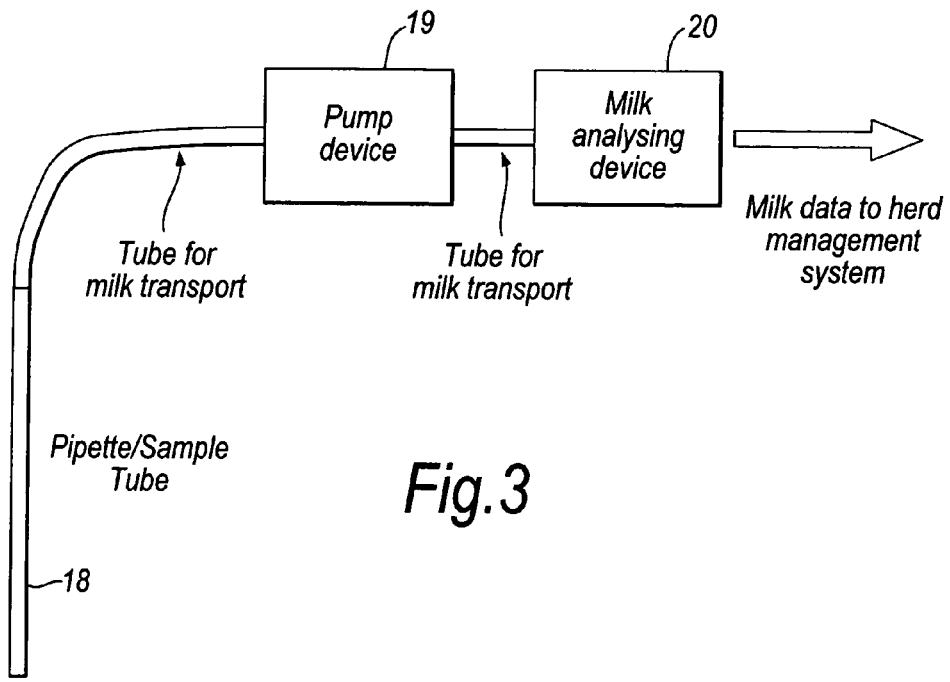
FIG. 3 is a schematic illustration of the sample taking and analysing system.

In accordance with the present invention a probe 15 extends through the cover of the casing 1 and down into the metering chamber 7, the probe terminating near the bottom of the measuring container 6. At its lower end the probe 15 carries two sensors 16, 17, namely one sensor comprising a pair of electrodes for sensing the electrical conductivity of the milk, and a second sensor having a light emitting diode and a photocell for sensing the light absorption characteristic of the milk in the metering chamber. Electric leads connected to the sensors extend along the probe 15, as does a tube 18 defining a sampling duct for removing small samples from the metering chamber 7. Other forms of sensor, such as a temperature sensor can be provided on the probe in addition to or in place of the conductivity and light absorption sensors described. The sampling tube takes form of a pipette or suction tube 18 and as illustrated in FIG. 3 is connected through a sampling pump 19 to a milk analyser 20. The analyser 20 performs an analysis of the milk composition, e.g. to determine fat and/or protein content or the presence of other constituents, and either records the results of the analysis or transmits this data to a separate recording device, such as a computer. The milk analyser or computer also records the results of conductivity and light adsorption measurements carried out using the sensors 16, 17 carried by the probe 15.

Figure 2:
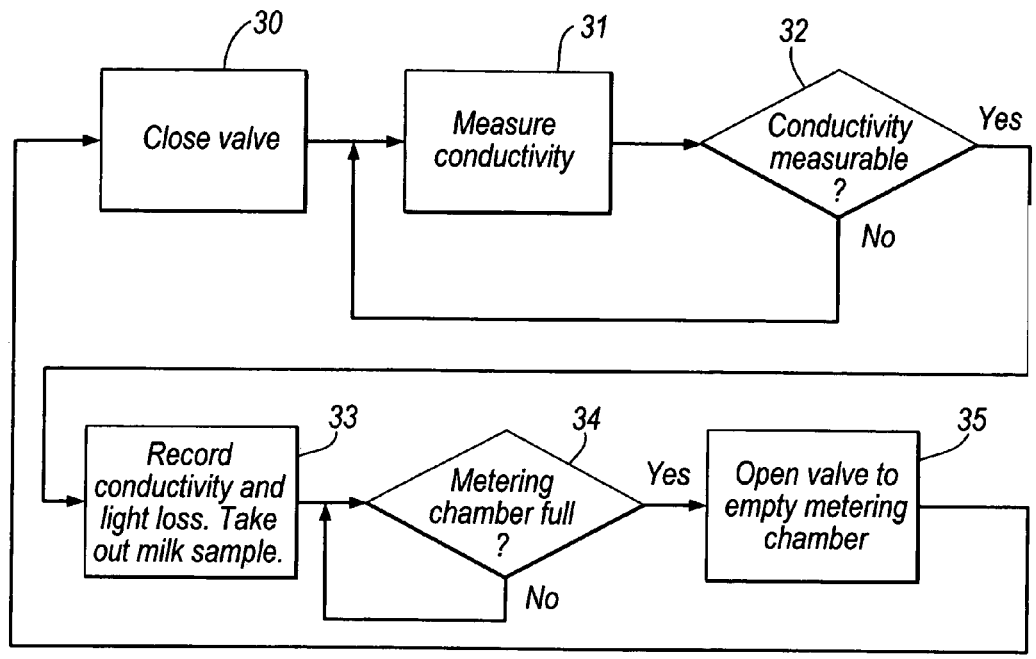
FIG. 2 is a flow chart illustrating the sequence of steps followed in the course of sampling and checking the milk during one filling and emptying cycle.

As already described, during the milking of an animal, the metering chamber 7 is repeatedly filled and emptied. FIG. 2 shows the sequence of steps conducted for sensing and recording data relating to the milk passing through the milk meter during each of the filling and emptying cycles. At the end of an emptying phase the control unit produces a signal to cause the valve actuator 9 to close the outlet valve 8 as indicated by step 30. The conductivity sensor is employed to check whether a conductivity measurement is possible and hence determine whether sufficient milk has collected in the metering chamber to immerse the lower end of the probe 15, an attempt to make conductivity measurement being made in step 31 and in step 32 it being checked whether the measurement has been successful. Steps 31 and 32 are repeated until it is confirmed that the conductivity measurement succeeded and the control sequence then advances to step 33 whereat the conductivity measurement is recorded, the light absorption characteristic is sensed and recorded, the number of the filling cycle is recorded, the time is recorded, and the sampling pump 19 is actuated to remove a milk sample from the metering chamber via the sampling tube 18, which sample is passed to the analyser 20 for analysis. In step 34 it is checked whether the predetermined weight of milk has been collected in the metering chamber 7, this being done repeatedly until the question is answered positively when, in step 35, the valve actuator 9 is operated to open the valve 8 to initiate the next emptying phase. The control cycle is then repeated and continues until the teat cup is detached from the teat of the animal and flow of milk into the milk meter ceases.

Figure 4:
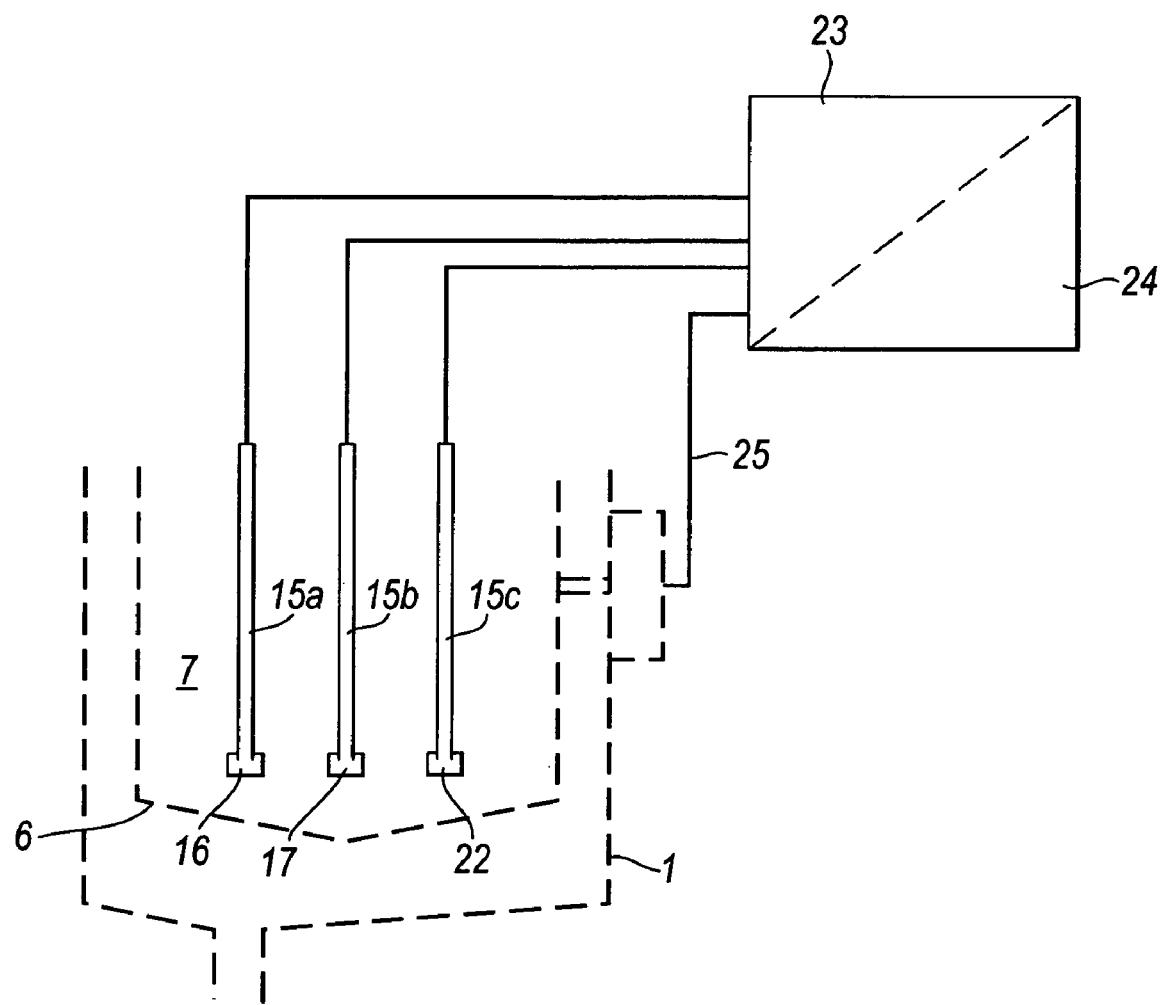
FIG. 4 is a schematic illustration of milk property sensing and recording arrangement.

FIG. 4 illustrates an arrangement in which three milk property sensors carried by probes 15a, 15b and 15c are positioned within the metering chamber 7, the sensors being a conductivity sensor 16 comprising electrodes, a light absorption sensor 17 comprising a light emitting diode and photocell, and a temperature sensor 22. Although the sensors are shown mounted on respective probes, two or more sensors can of course be provided on a common probe. The sensors are respectively connected to a control device 23 which is connected in turn to a recording device 24 for the output sensors to be transmitted to the control device and the measured values to be recorded by the recording device. The control device 23 and recording device 24 are conveniently combined in a common control and recording unit which may be a computer and preferably has the additional capability to compare recorded values measured by means of the sensors 16, 17, 22 under the control of the control device. The control device also has a connection 25 with the milk meter for the sensor readings to be coordinated with the filling and emptying cycles of the metering chamber 7. The control and recording unit can also serve to register and record the milk quantity determined by means of the milk meter. The arrangement of FIG. 4 can be used with or without a milk sampling arrangement such as that illustrated in FIG. 3. The same operational sequence as that described above with reference to FIG. 2 can be followed except of course that there may not be any sample taking, but there will be temperature readings taken at each step 33 during the filling and emptying cycles of the metering chamber.

Other structural and control arrangements are possible without departing from the scope of the invention. For example, the milk samples may be delivered to a sample collecting device arranged to collect them in tubes, phials or other suitable containers which can be provided within a cassette for transportation to a laboratory for analysis of the milk samples. Also, the taking of conductivity and/or light absorption measurements and/or the removal of samples from the metering chamber can be triggered by the control means in response to the strain gauge output signalling that a predetermined weight of milk has collected in the metering chamber 7. The latter control technique can reliably assure that data readings and/or samples are always taken at a certain defined point in the filing phase, or indeed at two or more defined points during the filling phase.

Thus, measurements and/or samples may be taken near the beginning, at the middle and/or at the end of the filling phase as desired.

From the foregoing description it will be understood that the invention allows extensive data to be collected over the course of a single milking. The recorded data can be compared with corresponding data from other milkings to help recognition of trends and changes which may assist herd management decisions about special treatment of individual animals and appropriate feeding levels. In addition, data collected during different filling and emptying cycles of the same milking procedure can be compared, which may be utilised, for example, for separation of foremilk. The recorded data related to milk obtained from respective udder quarters can also be compared and this may be useful for identification of subclinical mastitis or other conditions which may require treatment. It has been observed that some properties of milk, including conductivity and somatic cell count, are influenced by the time interval between successive milkings and for this reason the recording equipment is preferably adapted to record the time of milking and to calculate the interval since the immediately preceding milking of the same animal.

Some comparisons of data as described above can be performed automatically and the control equipment can be used to generate a signal to alert the farmer to a particular situation which requires attention e.g. as regards the health and well being of a particular animal. Furthermore, a screen may be provided for displaying recorded data and possible data comparisons to the farmer.

What is claimed is:

1. A method of milking an animal comprising the steps of directing milk collected from the udder of the animal into a metering chamber which is repeatedly filled and emptied during the milking procedure, checking at least one of the quality and the composition of the milk collected in the metering chamber, and counting the number of filling and emptying cycles of the metering chamber, characterised in that during each of at least several cycles of filling and emptying the metering chamber (1) the specific number of the cycle is recorded to thereby identify the stage in the course of milking during which the cycle has occurred, and (2) the quality or composition of the milk is checked by removing a milk sample from the metering chamber for analysis or by sensing and recording at least one property of the milk in the metering chamber, wherein the sensed and recorded property comprises at least one of electrical conductivity, a light absorption characteristic or temperature.

2. A method according to claim 1, wherein said milk sample is removed from the metering chamber and analysed to determine the somatic cell count, fat content, protein content, urea content or enzyme content thereof.

3. A method according to claim 1, wherein the milk sample is removed from the metering chamber through a tube.

4. A method according to claim 3, wherein the tube is a suction tube extending downwardly into the metering chamber.

5. A method according to claim 1, wherein electrical conductivity of the milk is sensed by electrodes carried by a probe extending into the metering chamber.

6. A method according to claim 1, wherein a light absorption characteristic of the milk is sensed by a light source and light detector carried by a probe extending into the metering chamber.

7. A method according to claim 6, wherein electrodes, the light source and the light detector are carried by the same probe.

8. A method according claim 6, wherein the light source comprises a light emitting diode and the light detector comprises a photocell.

9. A method according to claim 6, wherein a suction tube for removing a milk sample is incorporated in the probe.

10. A method according to claim 1, wherein properties of the milk in the metering chamber are sensed by sensors carried by two or more probes extending into the metering chamber.

11. A method according to claim 1, wherein recorded values relevant to the quality or composition of the milk collected in the metering chamber during a selected filling and emptying cycle are compared with the corresponding recorded values related to milk collected in the metering chamber during a corresponding filling and emptying cycle during a previous milking of the animal.

12. A method according to claim 1, wherein the recorded values relevant to the quality or composition of the milk collected in the metering chamber during a selected filling and emptying cycle are compared with the corresponding recorded values relating to milk collected in the metering chamber during an earlier filling and emptying cycle during the milking procedure.

13. A method according to claim 1, wherein the emptying of the metering chamber is commenced when a predetermined amount of milk has collected therein, the predetermined amount being not more than about 1 liter or about 0.5 kg.

14. A method according to claim 13, wherein the predetermined amount is selected in dependence upon the rate of flow of milk into the metering chamber.

15. A method according to claim 1, wherein emptying of the metering chamber is commenced when the amount of milk collected therein reaches a value in the range of from 20 g to 400 g.

16. A method according to claim 15, wherein the emptying of the metering chamber is commenced when the amount of milk collected therein reaches a value in the range of from 50 g to 150 g.

17. A method according to claim 1, wherein the time of milking is recorded and the interval since the immediately preceding milking of the animal is recorded.

18. A method according to claim 1, wherein the frequency of the filling and emptying cycles during which a milk sample is removed or milk property values are sensed and recorded is selected in dependence upon the results of the analysis of a sample removed or the milk property values sensed and recorded during a previous milking of the animal.

19. A method according to claim 1, wherein the frequency of the filling and emptying cycles during which a milk sample is removed or milk property values are sensed and recorded is selected in dependence upon the results of the analysis of a sample taken from the metering chamber or milk property values sensed and recorded during the milking procedure.

20. A method according to claim 1, wherein a milk sample is removed or milk property values are sensed and recorded during each filling and emptying cycle during at least part of the milking procedure.

21. A method according to claim 1, wherein the milk samples are removed from the metering chamber and are delivered directly to an analyser for analysis.

22. A method according to claim 1, wherein the milk samples removed from the metering chamber are delivered into sample collection containers and taken to a laboratory for analysis.

23. A method according to claim 1, wherein milk collected from respective teats of the udder of the animal is directed to respective milk metering chambers.

24. A method according to claim 23, wherein recorded values relevant to the quality or composition of the milk collected in the metering chambers connected to the respective teats of the animal are compared.

25. A milk metering apparatus comprising a metering chamber into which milk from an udder of an animal is delivered in the course of milking the animal, the metering chamber having a milk inlet and a milk outlet for repeated filling and emptying of the metering chamber during the milking procedure, the number of filling and emptying cycles being counted for determination of the milk quantity, and a sampling duct communicating with the interior of the metering chamber and defining an auxiliary milk outlet for separate removal of milk samples from the metering chamber during respective filling and emptying cycles.

26. An apparatus according to claim 25, wherein an analyser is connected to the milk sampling duct for receiving and analysing samples removed from the metering chamber.

27. An apparatus according to claim 26, wherein the analyser is operable to analyse the milk determining the somatic cell count, fat content, protein content, urea content or enzyme content.

28. An apparatus according to claim 25, wherein a sample collecting device is connected to the milk sampling duct for milk samples removed from metering chamber to be collected in sample containers.

29. An apparatus according to claim 25, wherein the sampling duct is connected to a suction device operable to remove a sample from the metering chamber by suction through the sampling duct.

30. An apparatus according to claim 25, wherein the sampling duct is formed in a tube extending downwardly into the metering chamber.

31. An apparatus according to claim 25, wherein at least one sensor is provided in the metering chamber for sensing a property of milk in the metering chamber, the milk property being electrical conductivity, a light absorption or transmission characteristic or temperature.

32. An apparatus according to claim 31, wherein a probe extending down into the metering chamber includes the sampling duct and carries the at least one sensor.

33. An apparatus according to claim 25, wherein the metering chamber is defined within a measuring container supported by a weighing device, and means are provided to cause removal of a sample from the metering chamber via the sampling duct in response to a signal from the weighing device.

34. An apparatus according to claim 33, wherein the weighing device comprises a strain gauge on which the measuring chamber is supported.

35. An apparatus according to claim 25, wherein the metering chamber has a milk collecting capacity not greater than 1 liter or 0.5 kg.

36. An apparatus according to claim 35, wherein the milk collecting capacity of the metering chamber is in the range of 20 to 400 g, preferably 50 to 150 g.

37. An apparatus according to claim 25, wherein a plurality of metering chambers are provided and are connected to respective teat cups.

38. An apparatus according to claim 37, including means to compare recorded values relevant to the quality or composition of the milk collected in the respective metering chambers.

39. A milk metering apparatus comprising a metering chamber into which milk from an udder of an animal is delivered in the course of milking the animal, the metering chamber having a milk inlet and a milk outlet for repeated filling and emptying of the metering chamber during the milking procedure, the number of filling and emptying cycles being counted for determination of the milk quantity, at least one sensor in the metering chamber for sensing a property of the milk in the metering chamber, the milk property being electrical conductivity, a light absorption or transmission characteristic or temperature, and recording means which records values of the at least one property sensed and compares these recorded values with corresponding sensed and recorded values.

40. An apparatus according claim 39, wherein the at least one sensor comprises electrodes for sensing the electrical conductivity of milk in the metering chamber.

41. An apparatus according to claim 39, wherein the at least one sensor comprises a light emitting device and a light detecting device for sensing a light absorption characteristic of milk in the metering chamber.

42. An apparatus according to claim 41, wherein the light emitting device comprises a light emitting diode and the light detecting device comprises a photocell.

43. An apparatus according to claim 39, wherein a plurality of sensors are located in the metering chamber, and two or more probes extend into the metering chamber and carry the sensors.

44. An apparatus according to claim 39, wherein recording means for recording property values of a milk sample or milk in the metering chamber records the number of the filling and emptying cycle during which the sample was removed from the metering chamber or the property values were sensed in the metering chamber.

45. An apparatus according to claim 44, wherein the recording means records the time of milking and the interval since the immediately preceding milking of the animal.

46. An apparatus according to claim 39, including control means arranged to control the frequency of the filling and emptying cycles during which a milk sample is removed from the metering chamber through the sampling duct or of milk property values are sensed and recorded.

47. An apparatus according to claim 46, wherein the control means is so arranged that the frequency set by the control means is dependent upon the results of a milk sample taken or milk property values sensed and recorded during a previous milking of the animal.

48. An apparatus according to claim 46, wherein the control means is so arranged that the frequency set by the control means is dependent upon the results of analysis of a milk sample taken or milk property values sensed and recorded during the same milking of the animal.

49. An apparatus according claim 39, wherein the at least one sensor comprises electrodes for sensing the electrical conductivity of milk in the metering chamber.

50. An apparatus according to claim 39, wherein the at least one sensor comprises a light emitting device and a light detecting device for sensing a light absorption characteristic of milk in the metering chamber.

51. An apparatus according to claim 50, wherein the light emitting device comprises a light emitting diode and the light detecting device comprises a photocell.

52. An apparatus according to claim 39, wherein a plurality of sensors are located in the metering chamber, and two or more probes extend into the metering chamber and carry the sensors.

53. An apparatus according to claim 39, wherein recording means for recording property values of milk in the metering chamber records the number of the filling and emptying cycle during which the property values were sensed in the metering chamber.

54. An apparatus according to claim 53, wherein the recording means records the time of milking and the interval since the immediately preceding milking of the animal.

55. An apparatus according to claim 39, including control means arranged to control the frequency of the filling and emptying cycles during which milk property values are sensed and recorded.

56. An apparatus according to claim 55, wherein the control means is so arranged that the frequency set by the control means is dependent upon the results of a milk sample taken or milk property values sensed and recorded during a previous milking of the animal.

57. An apparatus according to claim 55, wherein the control means is so arranged that the frequency set by the control means is dependent upon the milk property values sensed and recorded during the same milking of the animal.

\* \* \* \* \*